United States Patent
Shin et al.

(10) Patent No.: US 8,815,578 B2
(45) Date of Patent: Aug. 26, 2014

(54) CELL CULTURE TUBE AND MULTIPLE ROLLER TUBE CELL CULTURE APPARATUS INCLUDING THE SAME

(75) Inventors: Sung Ho Shin, Cheongju-si (KR); Jung Gyu Woo, Seoul (KR); Jai Myung Yang, Seoul (KR); Jai Jun Choung, Seoul (KR); Kyung Suk Kim, Seoul (KR); Mi Ran Choi, Seoul (KR)

(73) Assignee: Corestem Co., Ltd., Chungbuk (KR)

( * ) Notice: Subject to any disclaimer, the term of this patent is extended or adjusted under 35 U.S.C. 154(b) by 1169 days.

(21) Appl. No.: 12/596,693

(22) PCT Filed: Apr. 10, 2008

(86) PCT No.: PCT/KR2008/002028
§ 371 (c)(1),
(2), (4) Date: Oct. 20, 2009

(87) PCT Pub. No.: WO2008/130119
PCT Pub. Date: Oct. 30, 2008

(65) Prior Publication Data
US 2010/0136672 A1   Jun. 3, 2010

(30) Foreign Application Priority Data
Apr. 20, 2007   (KR) .................. 10-2007-0038846

(51) Int. Cl.
*C12M 3/04* (2006.01)
*C12M 1/24* (2006.01)

(52) U.S. Cl.
USPC .................. 435/298.2; 435/299.1; 435/299.2

(58) Field of Classification Search
USPC ........................... 435/298.2, 299.1
See application file for complete search history.

(56) References Cited

U.S. PATENT DOCUMENTS

| 4,228,242 | A  |   | 10/1980 | Girard et al. |
|-----------|----|---|---------|-----------|
| 4,310,630 | A  | * | 1/1982  | Girard et al. ............. 435/299.1 |
| 6,492,163 | B1 | * | 12/2002 | Yoo et al. .................... 435/298.2 |
| 6,605,463 | B1 | * | 8/2003  | Bader ........................ 435/298.2 |
| 2007/0298365 | A1 | * | 12/2007 | Xu ................................. 433/17 |

FOREIGN PATENT DOCUMENTS

| CN | 1883416 A | * | 12/2006 |
|----|-----------|---|---------|
| EP | 1260580   |   | 11/2002 |
| JP | 62044173  |   | 2/1987  |

OTHER PUBLICATIONS

English langauge machine translation of CN 1883416 (Dec. 27, 2006), pp. 1-9.*
International Search Report from PCT/KR2008/002028, dated Aug. 6, 2008.

* cited by examiner

*Primary Examiner* — William H Beisner
(74) *Attorney, Agent, or Firm* — Clark & Eling LLP

(57) ABSTRACT

Disclosed is a cell culture tube, having in opposite end walls two respective eccentric openings which communicate with each other through an inner straight passage formed in the cell culture tube, in which the inner straight passage is tilted at an angle relative to a longitudinal axis of the cell culture tube to allow a culture medium to smoothly flow into and out of the inner passage through the openings. Also, provided is a multiple cell culture system using a plurality of the culture tubes.

6 Claims, 3 Drawing Sheets

18

_US 8,815,578 B2_

CELL CULTURE TUBE AND MULTIPLE ROLLER TUBE CELL CULTURE APPARATUS INCLUDING THE SAME

CROSS-REFERENCE TO RELATED APPLICATIONS

This application claims priority under 35 U.S.C. §371 from international application PCT/KR2008/002028, filed Apr. 10, 2008, which claims priority from Korean Patent Application 10-2007-0038846, filed Apr. 20, 2007.

TECHNICAL FIELD

The present invention relates, in general, to a cell culture system for use in ex vivo culturing of animal cells and, more particularly, to a mass-scale cell culture system using a bundle of cell culture tubes suitable for use in ex vivo culturing of animal cells.

BACKGROUND ART

For effective animal cell culture, intensive attention has recently been paid to culture methods based on cell properties. As a result, culture methods suitable for hybridomas and embryonic stem cells have been developed and widely used. However, methods developed to date for mass-culturing adherent cells, such as fibroblastoid cells, epithelial-type cells and the like, have not yet been perfected, suffering from the disadvantages of having a low yield and requiring a long time period for mass-scale culture.

As a technique for overcoming these problems, a cell culture tube and a cell culture system using the same were proposed.

According to this conventional technique, the mass production of animal cells can be achieved by rotating a tube bundles assembled in roller drums installed inside a housing with the aid of a motor while feeding a culture medium at a constant rate into the drum to allow the culture medium to flow into the assembled tubes, so as to distribute the cells uniformly throughout the tube due to the revolution. For the detailed constitution of this culture system, reference may be made to Korean Patent Application No. 2001-0027831, which was filed by the present inventors.

The culture system, however, is disadvantageous in that because culture influx into the tubes assembled in the roller drum is different depending on the position thereof, culture environments are different from one tube to another, leading to difficulty in realizing uniform cell culture. Also, when cells and culture media flow in and out tubes through the openings located in opposite end walls of the tubes, membranes are formed over the openings due to surface tension, making it difficult for culture media to freely move through the openings. These problems are described in detail with reference to FIGS. 2 to 4.

FIG. 2 shows a conventional roller drum 4 in which cell culture tubes 1 in a bundle are assembled. When a predetermined amount of a culture medium is provided into the roller drum 4, it gathers at the bottom of the drum 4. While the roller drum 4 rotates around a central rotating shaft 3, the culture medium flows into each cell culture tube 1.

Referring to FIG. 3, a conventional cell culture tube 1 with openings 2 formed in the opposite end walls thereof is shown in a perspective view. The openings 2 are eccentrically located at corresponding positions in contact with the edge sides of the end walls, and serve as gates through which the culture medium can flow in and out. Formed parallel to the bottom of the cell culture tube, however, the openings 2 do not allow the culture medium to freely move therethrough when surface tension occurs to thus form a drop over the opening 2.

Turning to FIG. 4, the conventional cell culture tubes 1 contain a culture medium in different amounts depending on their distances from the central rotating shaft 3. For example, a tube 1a in the proximity of the central rotating shaft 3 contains a small a mount of the culture medium while a distal tube 1b contains a relatively large amount of the culture medium. This difference is because the angle between the level of the culture medium and the cell culture tubes 1a and 1b varies depending on the how far the tubes 1a and 1b are spaced apart from the central rotating shaft 3. The difference in culture medium amount between cell culture tubes 1a and 1b results in non-uniform cell culture in the cell culture tubes.

DISCLOSURE OF INVENTION

Technical Problem

Accordingly, the present invention has been made keeping in mind the above problems occurring in the prior art, and an object of the present invention is to provide a mass-scale cell culture system in which a culture medium is introduced in a constant amount into tubes irrespective of the positions of the tubes, so that a constant amount of the culture medium is allowed to flow into each tube in tube bundles so as to enable uniform cell culture throughout the tubes.

It is another object of the present invention to provide a cell culture tube which is designed to introduce thereinto and discharge therefrom a constant amount of the culture medium without the formation of a drop over the openings thereof due to surface tension.

Technical Solution

In order to accomplish the above objects, the present invention provides a cell culture tube 18, having at opposite end walls two respective eccentric openings which communicate with each other through an inner straight passage formed in the cell culture tube 18, said inner straight passage being tilted at an angle with respect to the longitudinal axis of the cell culture tube to allow a culture medium to smoothly flow in and out of the inner passage through the openings.

Preferably, the inner straight passage is tilted at an angle of 1-5 degrees.

In another preferable embodiment of the present invention, one of the two openings is located at a position in contact with the edge side of an end wall while the other is formed such that its circumference is spaced apart from the edge side of the tube 18.

In a further preferable embodiment, the cell culture tube 18 has a cross section selected from a group comprising a circle, an ellipse, and a polygon.

Also, each of the openings formed at the opposite end wall sides preferably has a size ranging from 1 to 70% of the cross-sectional area of the tube.

In accordance with another aspect of the present invention, there is provided a multiple roller tube cell culture apparatus, comprising: a cylindrical housing 14 for accommodating at least one drum 13, with a bundle of cell culture tubes 18 arranged therein, rotatable around a shaft 21 of the housing, said cell culture tubes 18 having two elliptical or semi-elliptical openings 19 formed in respective end walls thereof; a driving means 20 for rotating the drum 13; a medium reservoir 30 for storing fresh culture medium to be fed into the drum 13; and a harvest reservoir 40 for storing a culture product grown in the drum 13, wherein each of the cell culture tubes 18a, having two elliptical openings 19a in respective end walls thereof, is positioned near the shaft 21, and each of the cell culture tubes 18b having two semi-elliptical openings 19b in respective end walls thereof is arranged at a position distant from the shaft and near the inner circumference of the drum 13.

Further, the cell culture tube 18 used in the system has the structure described above.

Advantageous Effects

According to the present invention, a culture medium is introduced in a constant amount into the tubes irrespective of the positions thereof, so as to enable uniform cell culture throughout the tubes. In addition, having an inner passage tilted at an angle relative to the axis thereof, the cell culture tube is designed to introduce thereinto and discharge therefrom a constant amount of the culture medium without the formation of a drop over the openings thereof due to surface tension.

DESCRIPTION OF REFERENCE NUMERALS OF DRAWINGS

Figure 1:
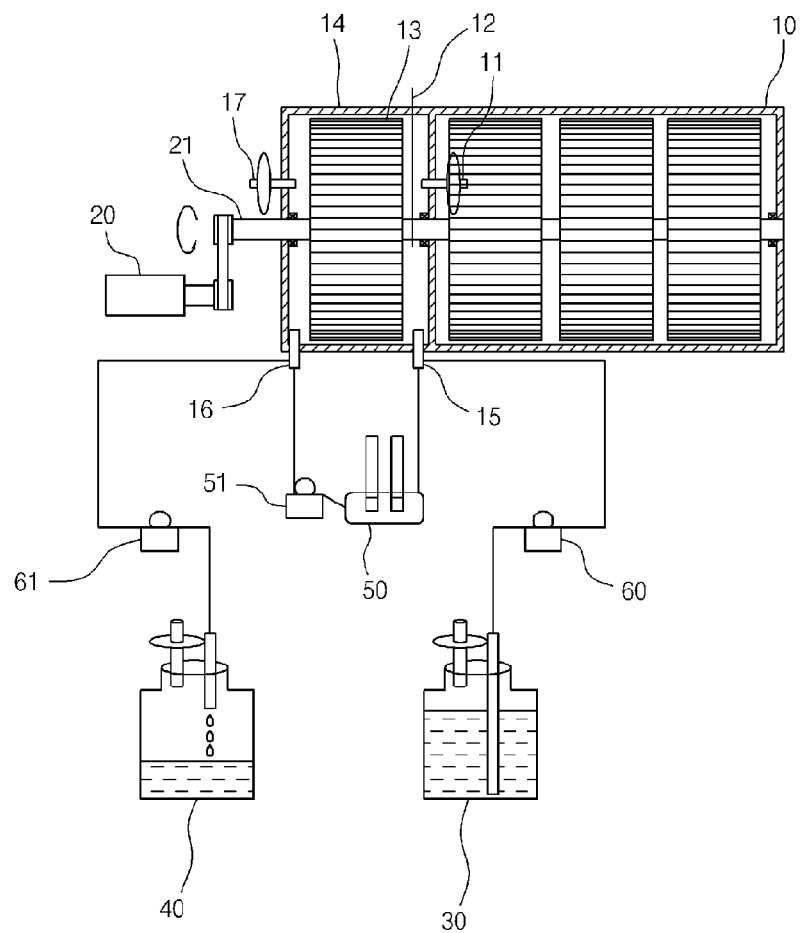
FIG. 1 is a schematic diagram showing a mass-scale cell culture system.
Figure 2:
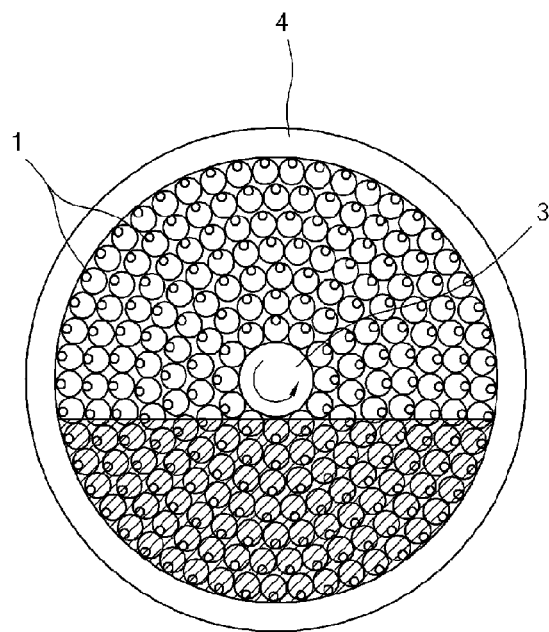
FIG. 2 is a schematic diagram showing a conventional tube bundle.
Figure 3:
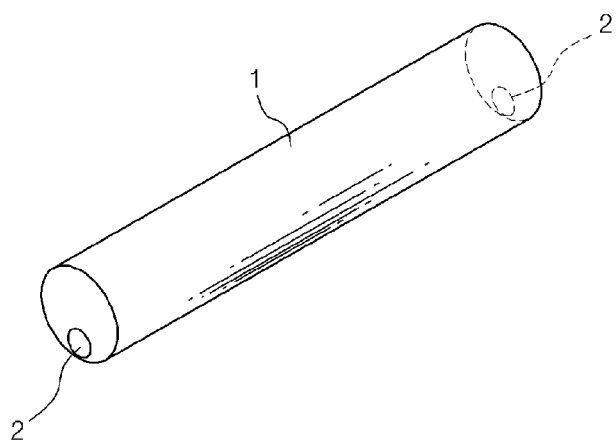
FIG. 3 is a perspective view of a conventional cell culture tube.
Figure 4:
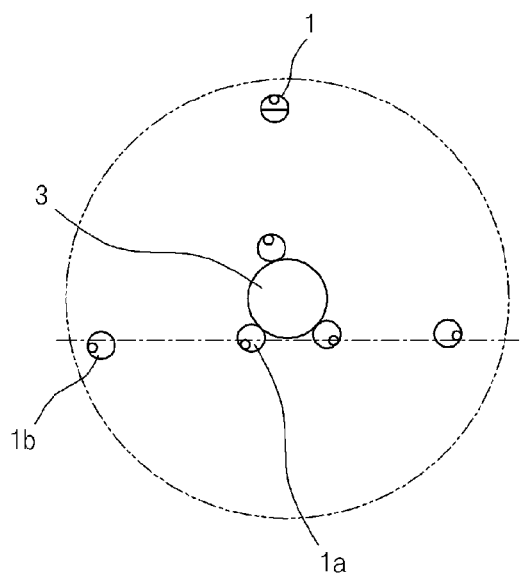
FIG. 4 is a conceptual diagram showing a problem with the conventional cell culture tube.

10: Multiple roller tube cell culture apparatus
13: Drum or tube bundle
14: Cylindrical housing 18: Culture tube
19: Opening 20: Driving means
30: Medium reservoir 40: Harvest reservoir
50: Oxygen and pH Sensors
60: Medium transfer pump

BEST MODE FOR CARRYING OUT THE INVENTION

The preferred embodiments of the present invention are best understood with reference to the accompanying drawings, wherein the same reference numerals are used throughout the different drawings to designate the same or like components.

FIG. 1 shows the structure of a mass-scale cell culture system according to the present invention, comprising: a multiple roller tube cell culture apparatus 10 containing one or more cell culture tube bundles 13 therein; a driving means 20 for revolving the tube bundles 13; a medium reservoir for storing a fresh culture medium to be fed into the multiple roller tube cell culture apparatus 10; and a harvest reservoir 40 for storing a culture product grown in the culture bundles 13.

In the multiple roller tube cell culture apparatus 10, an oxygen inlet 11 for introducing oxygen into the tube bundles 13 therethrough and an air outlet 17 for discharging air from the tube bundles 13 therethrough are formed. Also, the multiple roller tube cell culture apparatus 10 is provided with a medium inlet 15, through which a culture medium is introduced into the tube bundles 13, and a culture outlet 16, through which a culture is discharged from the tube bundles 13.

The driving means 20, for example, a motor, rotates the central rotating shaft 21 so that the tube bundles 13 are rotated along with the shaft.

In addition, a medium transfer pump 60 is installed to feed a cell culture medium from the medium reservoir 30 to the tube bundles 13, and a transfer pump 61 functions to transfer the culture product to the harvest reservoir. The cell culture system also has a plurality of sensors 50 for sensing the pH and dissolved oxygen level inside the housing 14 during a cell culturing process, with a circulation pump 51 provided for the sensors.

When the culture medium is fed from the medium reservoir 30 through the medium inlet 15 to the inside of the apparatus with the medium transfer pump 60, its feeding rate is controlled by a level controller 12 so as to automatically maintain the cell culture medium inside the housing 14 at a desired level. A harvest outlet 16 is provided for discharging the culture products from the housing 14 to the harvest reservoir 40 therethrough after the cell culturing process is finished. The oxygen and pH sensors 50 function to monitor the pH and dissolved oxygen level of the culture, a sample of which is transferred to the sensors by the circulation pump 51, thus indicating the state of the cultured cells. During the cell culturing process of the cell culture system, humidified and sterilized air is continuously fed into the housing 14 through the oxygen inlet 11 so as to provide an aerobic environment for the cells while gases generated inside the housing are smoothly discharged from the housing through the air outlet 17, thus maintaining a target oxygen level for the cells. When the cell culture tubes inside the housing are revolved at a speed of ⅓-¼ rpm around the central rotating shaft 21, the cell culture tubes are gradually brought into contact with the medium inside the housing. The medium is thus introduced into the cell culture tubes, and allows the cells to be stuck to the internal surface of the tubes and grow in the tubes. The cells inside the culture tubes grow through the metabolism of the nutrients of the media. The cell culture tubes with the eccentric openings formed in their end walls are arranged around the rotating shaft inside the housing such that the openings of the tubes are positioned outward in the radial direction of the housing. Therefore, when the tubes are revolved, the media contained in the housing smoothly flows into or from the tubes through the openings. When a cell suspension is introduced into the cell culture tube bundles, it generally takes 24-72 hours for the cells to completely attach on the internal surface of the tubes. When the cells are completely stuck to the internal surface of the tubes, the cell culture medium inside the tubes is distributed to the cells and changed with fresh medium. As for the medium exchange, its intervals are set in consideration of concentrations of nutrients, such as glucose, lactate, ammonia, etc. and pH levels, in order to afford the greatest production of cells. The cell culture medium inside the housing is automatically exchanged with fresh medium under the control of the level controller. The cell culturing process of the system is performed with an injection of humidified and sterilized gases including oxygen and carbon dioxide into the housing to adjust the pH and dissolved oxygen level of the culture. The mass-scale cell culture system according to the present invention thus automatically performs desired cell culture and analysis.

The mass-scale cell culture system according to the present invention can culture cells in a batch type, a continuous batch type or a continuous type, in which a medium is dispensed into culture tubes and in which a predetermined amount thereof is continuously exchanged with a fresh medium. Having the structure in which air is exchanged through the medium surface within each culture tube, the culture system of the present invention provides large air contact surfaces, compared to conventional culture systems, so that the cells are not under air bubble stress or shear stress, unlike conventional bioreactors. At cell surfaces in contact with air, the effective delivery of air into cells occurs, ensuring active glycolysis. In an oxygen-deficient condition, glucose, serving as an energy source, is decomposed into lactic acid to decrease the pH of the medium, which leads, in turn, to damage to the cells. On the other hand, in the presence of large amounts of dissolved oxygen, cells can obtain a large amount of energy through the TCA cycle (tricarboxylic acid cycle) with no decrease in pH. In addition, since glucose, an energy source, is rapidly depleted at the surface with which cells are in direct contact, cells tend to choose the TCA cycle in order to effectively use carbon sources. When these conditions are sustained for a long period of time, however, cells themselves are under stress. Cells can be restored to a normal state if they are placed in a medium in such a way as to bring the cell surface into contact with the medium, or are provided with fresh medium. This principle is the basis of the operation of a roller bottle, which is one of the most popular systems for culturing adherent cells at present. In addition to adopting the principle, the multiple roller tube cell culture apparatus of the present invention has improved air provision and pH control, requires only a very small culture space, and cultures cells in an automatic operation. Therefore, the culture system of the present invention overcomes the problems afflicting conventional roller bottles, that is, incapability of automatic operation and poor air exchange and pH control.

For information on such a mass-scale cell culture system, reference may be made to Korean Patent Application No. 2001-0027831, filed by the present inventors. The technical spirit of the present invention is focused on cell culture tubes 18 and the distribution of the tubes 18 in the tube bundle 13, which is described in detail below.

Figure 5:
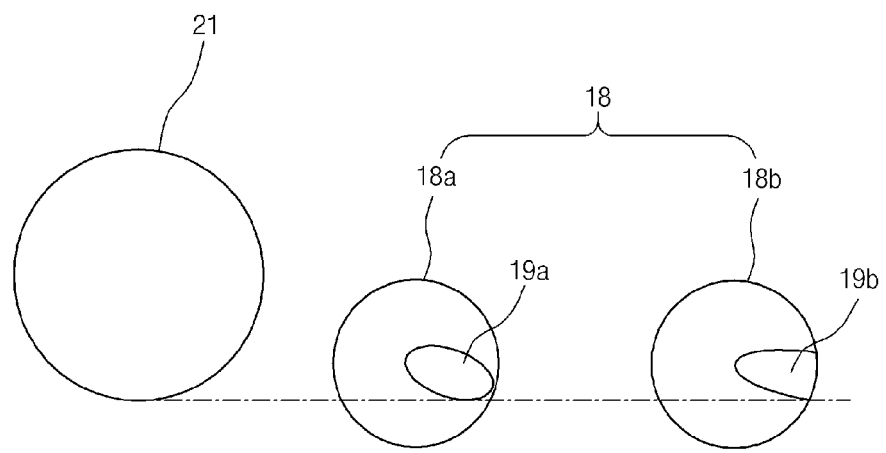
FIG. 5 is a conceptual diagram showing a tube bundle according to the present invention, which is a solution to the problem with the conventional cell culture tube.

With reference to FIG. 5, cell culture tubes 18 are arranged in a radial direction around the rotating shaft 21 within the tube bundle 13 (see FIG. 1). In the tube bundle 13 according to an embodiment of the present invention, tubes 18a having elliptical openings 19a are positioned near the rotating shaft 21, while tubes 18b having semi-elliptical openings 19b are arranged at positions distant from the shaft and near the inner circumference of the housing. Thus, the culture medium is uniformly distributed throughout the tubes 18a and 18b.

In FIG. 5, a tube bundle 13 is schematically shown in part to describe the relative positions of the tubes 18a and 18b from the rotating shaft 21. In FIG. 5, the dot and dash line indicates a constant level of the culture medium stored in the tube bundle 13. As seen in FIG. 5, the culture medium is introduced in a constant amount into the tubes 18a and 18b irrespective of the positions of the tubes 18a and 18b. Thus, a constant amount of the culture medium is allowed to flow into each tube 18 in the tube bundle 13 so as to enable uniform cell culture throughout the tubes.

The solutions to the problems encountered in the prior art are not limited to the elliptical openings 19a or semi-elliptical openings 19b. Examples of the semi-elliptical openings suitable for the present invention include long semi-elliptical openings and short semi-elliptical openings. As long as its surface area is not over 50% of the cross sectional area of the tube 18, the opening may have any elliptical or semi-elliptical shape.

Any structure is included within the spirit of the present invention as long as it allows a constant amount of the culture medium to flow into each of the tubes 18 irrespective of the level of the culture medium introduced into the tube bundle 13, in which many tubes 18 are assembled. The technical features of the present invention are also found in the angle and shape of the openings formed in the tube, which are designed to introduce a constant amount of the culture medium into each tube 18 when the tube bundle 13 is rotated around the rotating shaft 21.

Figure 6:
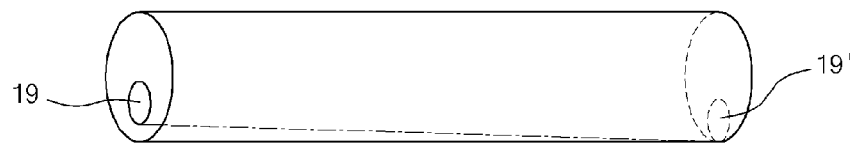
FIG. 6 is a schematic diagram showing a slope of an inner passage formed in the cell culture tube of FIG. 5.

With reference to FIG. 6, a detailed description is given of the structure of the tube 18.

The cell culture tube 18 according to an embodiment of the present invention may be in the form of a rod, and has at the opposite end walls two respective eccentric openings 19 which communicate with each other through an inner passage. Thus, the culture medium can flow in and out of the inner passage through the openings.

The tube 18 may have the cross section of a circle, an ellipse, a polygon, or the like. The number of culture tubes assembled in the tube bundle 13 may be determined depending on the cross-sectional shape thereof.

In order to solve the problem, encountered in the prior art, in which the culture medium cannot freely move through the openings when surface tension occurs, thus forming a drop over the opening 2, the tube 18 according to the present invention is formed to have an inner passage which extends from one opening to the other opening and which is tilted at a predetermined angle with the horizontal line when the tube is placed on the ground.

As shown in FIG. 6, one 19' of the two openings is located at a position in contact with the edge side of an end wall while the other 19 is formed such that its circumference is spaced apart from the edge side of the tube 18. In FIG. 6, reference numeral 19 indicates an 'inlet' through which a cell culture medium is introduced into the culture tube while reference numeral 19' indicates an 'outlet' through which a cell culture medium is discharged from the culture tube, and vice versa. In either case, a constant slope is formed between the inlet and the outlet. In this regard, the tube is formed in a manner such that the inner thickness of the tube varies at a constant rate along the inner passage to thus form a slope forming a predetermined angle with the bottom line. As shown in FIG. 6, the lower side of the passage, extending between the openings 19 and 19' has a constant slope at an angle relative to the bottom line of the tube 18, so that the culture medium more freely flows along the passage through the openings.

According to a conventional technique, the tube bundle has a tube arrangement in which tubes are tilted (0 to 5 degrees). However, it is difficult in practice to orient a plurality of tubes at the same slope. This problem can be overcome by the tube 18 which is provided with an inner slope according to an embodiment of the present invention. Preferably, the inner slope of the tube 18 ranges from 1 to 5 degrees, but is not limited thereto. Various slopes may be formed according to purposes of the designer.

Additionally, the size of each of the openings 19 and 19' formed at the opposite end wall sides is preferably 1 to 70% of the cross-sectional area of the tube. For example, when the openings 19 and 19' are small, the culture medium is introduced in a small amount into the tube. On the other hand, when the openings 19 and 19' are large, the culture medium is introduced in a large amount into the tube. Thus, the size of the openings must be determined in consideration of the types and amounts of the cells to be cultured.

The invention claimed is:

1. A cylindrical cell culture tube (18), having two openings which communicate with each other through an inner straight passage formed in the cell culture tube (18), wherein (a) the openings are eccentrically located on opposite ends of the cell culture tube (18), (b) the openings have an elliptical or semi-elliptical cross-section, (c) the inner straight passage extends between the two openings, (d) the inner straight passage is tilted at an angle of 1-5 degrees, and (e) said inner straight passage being tilted at an angle with a longitudinal axis of the cell culture tube to allow a culture medium to smoothly flow in and out of the inner passage through the openings, wherein one of the two openings is located at a position in contact with the side edge of an end wall of the cell culture tube and the other is located so that its circumference is spaced apart from the side edge of the other end wall of the cell culture tube.

2. The cell culture tube according to claim 1, wherein each of the openings formed in the opposite end walls has a size as large as 1 to 70% or a cross-sectional area of the tube.

3. A cylindrical cell culture tube (18), having two openings which communicate with each other through an inner straight passage formed in the cell culture tube (18), wherein (a) the openings are eccentrically located on opposite ends of the cell culture tube (18), (b) the openings have an elliptical or semi-elliptical cross-section, (c) the inner straight passage extends between the two openings, (d) one of the two openings is located at a position in contact with the side edge of an end wall while the other opening is formed such that its circumference is spaced apart from the side edge of the tube, and (e) said inner straight passage being tilted at an angle with a longitudinal axis of the cell culture tube to allow a culture medium to smoothly flow in and out of the inner passage through the openings.

4. The cell culture tube according to claim 3, wherein each of the openings formed in the opposite end wall sides has a size as large as 1 to 70% of a cross-sectional area of the tube.

5. A cylindrical cell culture tube (18), having at opposite end walls two respective eccentric openings which communicate with each other through an inner straight passage formed in the cell culture tube (18), said straight passage being tilted at an angle of 1-5 degrees with a longitudinal axis of the cell culture tube to allow a culture medium to smoothly flow in and out of the inner passage through the openings, wherein the openings have an elliptical or semi-elliptical cross-section, wherein one of the openings is located at a position in contact with the side edge of an end wall and the other is located so that its circumference is spaced apart from the side edge of the cell culture tube.

6. The cell culture tube according to claim 5, wherein each of the openings formed in the opposite end wall sides has a size as large as 1 to 70% of a cross-sectional area of the tube.

* * * * *